United States Patent
Baldi Coll et al.

(10) Patent No.: US 10,067,085 B2
(45) Date of Patent: Sep. 4, 2018

(54) ION SENSOR BASED ON DIFFERENTIAL MEASUREMENT, AND PRODUCTION METHOD

(71) Applicant: CONSEJO SUPERIOR DE INVESTIGACIONES CIENTIFÍCAS (CSIC), Madrid (ES)

(72) Inventors: Antoni Baldi Coll, Barcelona (ES); Carlos Dominguez Horna, Barcelona (ES); Cecilia Jimenéz Jorquera, Barcelona (ES); César Fernández Sánchez, Barcelona (ES); Andreu Llobera Adan, Barcelona (ES); Ángel Merlos Domingo, Barcelona (ES); Alfredo Cadarso Busto, Barcelona (ES); Isabel Burdallo Bautista, Barcelona (ES); Ferrán Vera Gras, Barcelona (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 0 days.

(21) Appl. No.: 15/113,381

(22) PCT Filed: Jan. 29, 2015

(86) PCT No.: PCT/ES2015/070063
§ 371 (c)(1),
(2) Date: Jul. 21, 2016

(87) PCT Pub. No.: WO2015/121516
PCT Pub. Date: Aug. 20, 2015

(65) Prior Publication Data
US 2017/0010237 A1    Jan. 12, 2017

(30) Foreign Application Priority Data
Feb. 11, 2014    (ES) .................................. 201430180

(51) Int. Cl.
*G01N 27/403*    (2006.01)
*G01N 27/414*    (2006.01)
(Continued)

(52) U.S. Cl.
CPC ........... *G01N 27/414* (2013.01); *H01L 21/78* (2013.01); *H01L 23/3157* (2013.01);
(Continued)

(58) Field of Classification Search
CPC ............ G01N 27/414; G01N 27/4148; G01N 27/4167
See application file for complete search history.

(56) References Cited

U.S. PATENT DOCUMENTS 4,502,938 A * 3/1985 Covington ......... A61B 5/14542
204/403.06
4,874,499 A   11/1989 Smith et al.
(Continued)

FOREIGN PATENT DOCUMENTS

EP    0155725 A1    2/1985

OTHER PUBLICATIONS

Jae Ho Shin, et al: "ISFET-Based Differential PC02 Sensors Employing a Low-Resistance Gas-Permeable Membrane", Analytical Chemistry, American Chemical Society, US, vol. 68, No. 18, Sep. 15, 1996 (Sep. 15, 1996), pp. 3166-3172.
(Continued)

*Primary Examiner* — Frederick B Hargrove
(74) *Attorney, Agent, or Firm* — Leason Ellis LLP

(57) ABSTRACT

Ion sensor based on differential measurement comprising an ISFTET-REFET pair wherein the REFET is defined by a structure composed of an ISFET covered by a microreservoir where an internal reference solution is contained. The sensor comprises a first and a second ion-selective field effect transistor, an electrode, a substrate on the surface
(Continued)

whereof are integrated the two transistors, connection tracks and the electrode and a structure adhered on the first ion-selective field effect transistor which creates a micro-reservoir on the gate of said first transistor, with the micro-reservoir having a microchannel which connects the micro-reservoir with the exterior and the microreservoir being filled with the reference solution.

19 Claims, 5 Drawing Sheets

(51) Int. Cl.
  *H01L 21/78* (2006.01)
  *H01L 23/31* (2006.01)
  *H01L 27/12* (2006.01)
(52) U.S. Cl.
  CPC .................... *H01L 27/1203* (2013.01); *H01L 2224/48091* (2013.01); *H01L 2224/8592* (2013.01); *H01L 2924/16235* (2013.01)

(56) References Cited

U.S. PATENT DOCUMENTS

| | | | |
|---|---|---|---|
| 5,250,168 | A | 10/1993 | Tsukada et al. |
| 2003/0214005 | A1* | 11/2003 | Chou .................... G01N 27/414 257/428 |
| 2013/0069120 | A1* | 3/2013 | Merz .................. G01N 27/4148 257/253 |
| 2013/0158378 | A1* | 6/2013 | Berger ............... A61B 5/14546 600/348 |
| 2014/0264464 | A1* | 9/2014 | Fife .................... G01N 27/4145 257/253 |

OTHER PUBLICATIONS

Arquint PH, et al: "Integrated blood-gas sensor for $pO_2$, $pCO_2$ and pH", Sensors and Actuators B: Chemical: International Journal Devoted to Research and Development of Physical and Chemical Transducers, Elsevier S.A, CH, vol. 13, No. 1-3, May 1, 1993 (May 1, 1993), pp. 340-344.

Schoot Van Der B H et al: "A Flow Injection Analysis System With Glass-Bonded ISFETS for the Simultaneous Detection of Calcium and Potassium Ions and PH", Sensors and Actuators B: Chemical: International Journal Devoted to Research and Development of Physical and Chemical Transducers, Elsevier S.A, CH, vol. B04, No. 3/04, Oct. 1, 1990 (Oct. 1, 1990), pp. 239-241.

Ravezzi L, et al: "A CMOS ASIC for differential read-out of ISFET sensors", Electronics, Circuits and Systems, 2001 ICECS 2001. The 8th IEEE Inte Rnational Conference on Sep. 2-5, 2001, Piscataway, NJ, USA,IEEE, Piscataway, NJ, USA, A vol. 3, Sep. 2, 2001, (Sep. 2, 2001), pp. 1513-1516.

Woias P, et al: "An ISFET-FIA system for high precision pH recording", Sensors and Actuators B: Chemical: International Journal Devoted to Research and Development of Physical and Chemical Transducers, Elsevier S.A, CH, vol. 15, No. 1-3, Aug. 1, 1993 (Aug. 1, 1993), pp. 68-74.

Gumbrecht, W. et al., "Integrated blood gas sensor for $pO_2$, $pCO2$, pH sensor system for online blood monitoring", Sensors and Actuators B, Apr. 1994, vol. 19, No. 18-19, pp. 704-708.

International Search Report and Written Opinion in corresponding PCT Application No. PCT/ES2015/070063, dated Jan. 6, 2015.

International Preliminary Report on Patentability in corresponding PCT Application No. PCT/ES2015/070063, dated Aug. 16, 2016.

Sentron SI line pH probe manual, SENTRON, Oct. 2013, pp. 4-10.

Yang, H. et al. A pH-ISFET based micro sensor system on chip using standard CMOS technology. Proceedings—Fifth International Workshop on System-on-Chip for Real-Time Applications, IWSOC 2005, vol. 2005, pp. 180-18.

P.A. Comte, et al., A field effect transistor as a solid-state reference electrode, Analyt. Chimica Acta, 101 (1978) pp. 247-252.

Jae Ho Shin, et al., ISFET-Based Differential pCO2 Sensors Employing a Low-Resistance Gas-Permeable Membrane, Anal. Chem. 1996, 68, pp. 3166-3172.

* cited by examiner

ION SENSOR BASED ON DIFFERENTIAL MEASUREMENT, AND PRODUCTION METHOD

CROSS-REFERENCE TO RELATED PATENT APPLICATIONS

This application is a U.S. National Phase Application under 35 U.S.C. § 371 of International Patent Application No. PCT/ES2015/070063, filed Jan. 29, 2015, and claims the priority of P201430180, filed Feb. 11, 2014, all of which are incorporated by reference in their entireties. The International Application was published on Aug. 20, 2015 as International Publication No. WO 2015/121516.

OBJECT OF THE INVENTION

The present invention relates to an ion sensor based on differential measurement and to the manufacturing method thereof. Said sensor performs the measurement of the concentration of certain ions in a solution using ISFET (ion-selective field effect transistor) transistors and it compares said measurement with that of a reference solution which is stored in a microreservoir, performing said measurement via an ISFET transistor whose gate is kept in contact with said reference solution, also called REFET transistor (field effect transistor which does not respond to the ion concentration), and which, therefore, has zero response to the ions which are to be measured.

The technical field wherein the present invention is included is that of the sector of physical technologies and its more typical application is for ion measurement, for example, pH (concentration of hydrogen ions in a solution), in various sectors such as the food industry and biomedicine.

BACKGROUND OF THE INVENTION

In the current state of the art, the measurement of concentrations of various ions of a medium is performed in highly varied ways. One of the most widely used techniques is the use of test strips. These test strips are strips of paper with different areas which become coloured in contact with aqueous solutions, taking on different colours depending on the concentration of specific ions of the measurement solution. To identify the concentration of ions of the solution, after wetting the strip therewith, the user must compare the colours obtained with those of a table provided by the manufacturer. The result of this measurement technique greatly depends on the correct manipulation by the user and factors such as: the presence of proteins in the samples, the reaction time of the strip with the samples, or the homogeneity of the samples. An incorrect manipulation generates many false results (positive and negative). Furthermore, it is generally considered that the resolution of this technique is of 0.5 units, for the specific case of pH measurement, which lacks sufficient diagnostic value to take clinical decisions in some biomedical applications such as in Urolithiasis (Kwong T. et al. "Accuracy of urine pH testing in a regional metabolic renal clinic: is the dipstick enough?Urolithiasis 2013).

The standard measurement technique of ion concentration is atomic absorption. However, this technique requires a complex installation and its miniaturization is not feasible.

Ion Selective Electrodes (ISEs) are used for simpler measurements in terms of equipment and are less expensive. These electrodes have a selective membrane so that, by the exchange or interaction of the solution ions with the membrane, the ion activity becomes an electric potential. The selective membrane may be of several types, of glass, crystalline or based on ion-exchange compounds. The latter have a polymer (e.g. polyvinyl chloride, PVC) which immobilizes the ion selective compound. The measurement of the electric potential of the ISEs requires the use of a reference electrode, which is frequently integrated in the very body of the ISE (combined electrodes). The reference electrode is generally a metal electrode immersed in a reference solution which is in turn connected to the solution to be measured through a liquid bond. The main characteristic of the reference electrode is that its potential, i.e. the potential between the interior of the metal and the inside of the solution wherein it is immersed, does not depend on the composition of said solution. The reference electrodes usually have losses of reference solutions through the liquid bond, so that a periodic refilling thereof is required.

To obtain precise measurements, these electrodes require a prior calibration which consists of the measurement of the potential generated when the electrode is immersed in a known ion concentration solution. These electrodes form part of an instrument, which in the case of the pH is known as pHmeter, which is not cheap to manufacture, nor is it portable or autonomous and it requires specific maintenance and cleaning conditions for its correct conservation. The result of this measurement technique also depends on the correct manipulation by the user (who must be suitably trained for said purpose). An incorrect manipulation or conservation of the electrodes may give rise to false results.

Another type of sensors used for this class of measurements are the ISFET (ion-selective field effect transistor)-type sensors. These are devices manufactured using microelectronic technology. The potential of the solution (which is the transistor gate potential) is controlled by a reference electrode such as those used for the measurement with ISE-type electrodes. The ISFET is a field effect transistor whose threshold voltage varies with the ion concentration of the solution in contact with its gate dielectric. For many types of dielectrics ($SiO_2$, $Si_3N_4$, $Al_2O_3$, $Ta_2O_5$, $ZrO_2$), the variation of threshold voltage of the ISFET mainly depends on the $H^+$ ion and, therefore, it is used as pH sensor. To make sensors of other ions based on the ISFET, an additional layer called selective membrane as disclosed in U.S. Pat. No. 5,250,168 is deposited on the gate dielectric layer. Depending on the membrane deposited, the ISFET would function as a sensor for specific ions or others. The measurement with these sensors consists of recording the changes in threshold voltage of the field effect transistor, which are proportional to the changes in ion concentration that one wants to measure. A way of measuring the changes in threshold voltage of the ISFET is using a circuit which polarizes the device with a constant drain current and a constant source drain voltage. In this way, the changes in gate voltage the circuit applies to maintain said polarization are equal to the threshold voltage changes suffered by the ISFET. Therefore, the gate voltage applied by the circuit is taken as output signal.

Both the measurement systems based on ISE electrodes and those based on ISFET require a reference electrode to be able to measure the ions. This makes them expensive and requires periodical maintenance. In 1978, a solution was disclosed for pH measurement with ISFET-type devices without reference electrode (P. A. Comte and J. Janata, "A field effect transistor as a solid-state reference electrode", Analytica Chimica Acta) which consisted of the differential measurement of an ISFET and a REFET. In this case the REFET is formed by an ISFET the gate whereof is kept exposed to a constant pH. The differential measurement consists of measuring the threshold voltage of both devices using a single electrode immersed in the solution as terminal gate and obtaining the answer as subtraction of the two values obtained. The REFET gate is maintained exposed to a constant pH by the incorporation of a microreservoir filled with reference solution (internal solution). Said microreservoir is connected to the exterior via a microchannel which acts as liquid bond, so that the difference in potential between the external solution and the reference solution is small and is not greatly influence by the pH or the concentration of other ions in the external solution. In this way, the changes in potential which occur between the electrode and the solution are transferred to both threshold voltage values, and therefore have no impact on the differential value (they are cancelled in the subtraction operation). For this reason, the different measurement system can be implemented with any conductor electrode, without the need for it to be reference. Given that the REFET is exposed to a constant pH solution, the variation in the differential value shall be equivalent to the ISFET's response to the change in pH. However, the way of manufacturing the REFET described by Compte and Janata is difficult to automate and would therefore not make it possible to manufacture the sensors at a cost greatly less than those of the ISFETs with reference electrode, which would not allow its price to be accessible to the general public. Furthermore, in the design of the ISFET-REFET sensor described by Compte and Janata, the REFET's microreservoir is constructed with an epoxy resin. This microreservoir, once the resin has been cured, is filled with an agarose gel prepared in a buffer solution. Subsequently, a glass capillary is introduced, which acts as a microchannel, in the agarose gel and the microreservoir is sealed with a layer of epoxy resin. Thus, the sensor is stored dry; the buffered solution of the microreservoir is slowly evaporated through the microchannel, being replaced by air. The presence of air interior the microreservoir prevents it functioning correctly when it is used after an extended time has passed of immersion in aqueous solution. This is due to the fact that the filling with water, as well as the necessary diffusion of the trapped air to the exterior, is solely performed through the microchannel, which is not filled with hydrogel. Furthermore, the lifetime of this type of sensor depends on the volume of the microreservoir and on the dimensions of the microchannel which connects it with the exterior, since the reference solution in the microreservoir shall be diluted and contaminated through the microchannel, so that the error in the measurement may progressively increase a measurement that the pH of said solution varies with respect to its original value. For this reason, it is considered a sensor with a short lifetime.

Document EP 85200263 discloses a sensor wherein use is made of two ISFET sensors, one of which is found interior a conduit wherethrough the reference solution flows. In this way, said ISFET is always in contact with an uncontaminated solution. However, for this it is necessary to incorporate in the sensor a reference solution injection system as well as the means of supply of the injection system which make the solution described more complex and expensive.

Thus the state of the art has the following associated problems: the test strips are imprecise; the glass electrodes are expensive, fragile, require maintenance and cannot easily be miniaturized; the current ISFET and ISE-type sensors are miniaturizable but are expensive and require maintenance as they must be used with a reference electrode; the ISFET-REFET sensor proposed by Compte and Janata is expensive to manufacture and has a short lifetime; and the sensor disclosed in EP 85200263, in addition to concerning two ISFET transistors, has a greater cost and complexity due to the need to have a reference solution injection system.

DESCRIPTION OF THE INVENTION

The present invention discloses a novel ion sensor based on differential measurement comprising at least one ISFET transistor and a REFET transistor. The REFET is defined by a structure composed of an ISFET covered by a microreservoir where an internal reference solution is contained. A second object of the present invention is the manufacturing method of the sensor previously described which allows its mass production at low cost. A third object of the present invention is the sensor previously described immersed in a conditioning receptacle filled with the reference solution, which makes it possible to extend the useful life of said sensor.

Thus the first object of the present invention is an ion sensor based on differential measurement. Said sensor is characterized in that it at least comprises:

a first ion-selective field effect transistor and at least one second ion-selective field effect transistor, electrically connected by connection tracks to a measurement circuit;

an electrode of a conductor material;

at least one chip on the surface whereof are integrated the two field effect transistors. The chips shall preferably be of a semiconductor material;

a structure coupled on the first transistor configured to create a microreservoir on the gate of said first transistor and at least one microchannel which connects the microreservoir with the exterior, the microreservoir and the microchannel being filled with a reference solution. This structure adhering to the first field effect transistor is what creates the REFET; and, a substrate whereon are integrated the chips, the connection tracks and the electrode;

an encapsulating material which electrically insulates the connection tracks and partially insulates the first and second transistor of the solution to measure. This encapsulating material avoids that a flow of electrical current is produced between the solution (which together with electrode form the gate terminal) and another terminal of the transistor (drain, source or substrate).

It has been provided, in a particular embodiment of the invention, that the sensor described here integrates a single REFET and a plurality of selective ISFETs, each one of them to a different ion. This is achieved by having a series of selective membranes disposed in each ISFET so that each one of them detects a different ion. Both the ISFET and the REFET may be in the same chip or different chips, but all the ISFETs perform the differential measurement with respect to the same REFET. Thus it is possible to achieve, with a single sensor, a plurality of measurements of concentrations of different ions at the same time.

In a particular embodiment of the invention, the reference solution is contained in a hydrogel which occupies the volume of the microreservoir and the microchannel.

The REFET is preferably constructed from a H+ ion selective ISFET, with the reference solution being a buffer which fixes the pH at a determined value, but it also proposes that the REFET is constructed from an ISFET selective to another ion, i.e. that it includes a membrane selective to said ion on its gate dielectric, in which case the reference solution must contain a determined concentration of said ion.

In another particular embodiment of the invention, the first ion-selective field effect transistor is integrated in a first chip and at least one second ion-selective field effect transistor is integrated in a second chip. If there is a plurality of second transistors, each one of them could be integrated in an independent chip or they could all be integrated together in a single chip.

In another particular embodiment of the invention, it has also been provided that the first ion-selective field effect transistor and the at least one second ion-selective field effect transistor are integrated in the same chip. Thus it manages to reduce the manufacturing time and costs of the sensor. In another particular embodiment of the invention, the field effect transistors, the connection tracks, the electrode and a part of the measurement circuit are integrated in the same chip. Thus it manages to further reduce the manufacturing costs of the sensor and reduce its size considerably, which may be important for certain applications.

In another particular embodiment of the invention, the connection of the chips, more specifically of the connection "pads" of the chips, with the connection tracks is performed via wire bonding.

In another particular embodiment of the invention, the chips are encapsulated by a polymer, with the wires and the connection tracks being covered by said polymer and the gates of the first and second ion-selective field effect transistor, the outlet of the microchannel and the electrode being uncovered.

In another particular embodiment, it has been provided that the outer walls of the microreservoir of the first transistor (REFET) are, at least partially, of a material permeable to water molecules in gas phase and to air but not to the solution with the reference pH. Thus, the diffusion of the air molecules towards the exterior and of the water molecules towards the interior is performed throughout the surface of said permeable material accelerating the tuning process of the sensor when it is going to make use of it after a period in which it has not been used. In this way, it allows the dry storage of the sensor and a fast rehydration of the microreservoir before its use by the immersion in a conditioning solution. This obviously very considerably lengthens the useful life of this type of sensors.

In another particular embodiment of the invention an ion-selective membrane is placed on the gate of the at least one second transistor (ISFET). Thus, depending on what type of ions the membrane placed is selective to the ion sensor based on differential measurement object of the present invention can measure concentrations of different ions. In this way it is possible to obtain sensors to measure concentrations of different ions such as $Ca^{2+}$, $K^+$, $Na^+$, $Cl^-$, $NH_4^+$ or $CO_3^{2-}$.

In another particular embodiment of the sensor object of the present invention, the microreservoir has a volume between 0.001 $mm^3$ and 1 $mm^3$ and the microchannel has a section of between 1 square micrometer and 10000 square micrometers and a length between 10 microns and 1 mm. The concentration of chemical species interior the microreservoir follows an exponential evolution as these species diffuse through the microchannel towards the exterior. The time constant of that concentration variation is proportional to the section of the microchannel and inversely proportional to the volume of the microreservoir and the length of the microchannel. Therefore, the time taken to lose a certain quantity of the chemical compounds of the buffer which maintain the concentration of ions of the solution in the interior of the microreservoir and the degree of contamination of said solution with compounds from the exterior, is proportional to the section of the microchannel and inversely proportional to the volume of the microreservoir and to the length of the microchannel. In other words, a longer and/or finer microchannel provides a stable sensor signal during a longer time. However, a longer and finer channel also involves a greater electrical resistance of the microchannel filled with solution. As the microchannel must electrically connect the solution of the interior of the reservoir with the solution of the exterior to transmit the potential of the electrode to the REFET transistor gate, the greater the resistance of the microchannel, the greater the susceptibility of the sensor to electrical interference. This limits the dimensions of the microchannel and therefore the stable measurement time that can be obtained with the given dimensions of the microreservoir.

In another particular embodiment of the invention, it has been provided that there are 2 or more microchannels that connect the microreservoir with the exterior. Increasing the number of microchannels may allow reducing the section thereof without increasing the electrical resistance between the solution of the microreservoir and the solution to measure. A sufficiently reduced section of the microchannels avoids the intake of certain microorganisms in the interior of the microreservoir which could alter the characteristics of the reference solution of the surface of the REFET gate dielectric.

In another particular embodiment of the invention, it has been provided that removable and external sealing means are disposed, such as, for example, adhesive tape or similar, in the outlet of the microchannel to seal the content of the reservoir and the microchannel. The adhesive tape has the suitable form to be able to be manually removed. This makes it possible to lengthen the useful life of the sensor since the solution within the REFET is insulated, avoiding it from evaporating, until the first use of the sensor. Additionally, the material from which the structure which creates the microreservoir has been manufactured shall not be permeable to the reference solution.

In another particular embodiment of the invention, the structure which creates the microreservoir is at least partially of a gas permeable polymer, such as, for example, polydimethylsiloxane, which makes it possible to store the sensor dry allows using it after a few hours of soaking. This advantage is important to facilitate the storage and marketing of the sensor or to facilitate the transport thereof in the event that it is used in a portable measuring apparatus.

A second object of the present invention is the manufacturing method of the ion measurement sensor based on differential measurement described above. Said method at least comprises the following phases:

disposing equally spaced a plurality of first ion-selective field effect transistors on a first wafer;

coupling, preferably by bonding, a structure of bondable material on the first wafer, creating a plurality of equally spaced microreservoirs and microchannels in correspondence with the first ion-selective field effect transistors, so that each microreservoir is situated in correspondence and aligned with each first ion-selective field effect transistor;

cutting the first wafer in chips, where each chip comprises a first field effect transistor and a structure with a microreservoir and at least one microchannel;

bonding on a substrate the first ion-selective field effect transistor with the microreservoir and the microchannel, a second ion-selective field effect transistor, the electrode and the connection tracks;

connecting the connection tracks to the first and second transistor and encapsulating said first and second transistor and the connection tracks.

For the case wherein the first and second ion-selective field effect transistor are integrated in the same chip, the second wafer of bondable material has at least one orifice in proximity to each microreservoir, so that each orifice during the bonding phase is placed in correspondence with the gate of a second field effect transistor leaving exposed to the exterior said gate of the second transistor so that it is in contact with the solution to measure.

In a particular embodiment of the method object of the present invention, the coupling phase of the structure on the first wafer comprises adding a plurality of layers of bondable material previously subjected to a photolithography process on the first wafer, to generate the structure with the microreservoir and the microchannels.

In another particular embodiment of the method object of the present invention, the coupling phase of the structure on the first wafer comprises previously subjecting the structure of bondable material to a recessing process for the creation of the microreservoirs and the microchannels. This recessing process may be by vacuum, extrusion or similar of a second wafer.

In another particular embodiment it has been provided that the microchannel is integrated in the chip by a longitudinal recessing in the surface of the first wafer, i.e. of the chip. In this way, the structure of the REFET is completed by the bonding of a second wafer since it only contains now the reservoirs, or by the addition of layers of bondable and photolithographiable material on the ISFETs, to form the walls of the microreservoir and the covers of said microreservoirs.

It has been provided to deposit a layer of insulating material on the surface of the first and second field effect transistor to insulate the drain and the source of the first and second field effect transistor and the substrate of the solutions. Thus, only the gate of the first and second field effect transistor remains in contact with the solutions, both reference and that in which one wants to know the ion concentration. In another embodiment of the invention, encapsulating material is additionally deposited on all the edges of the first and second ion-selective field effect transistor to electrically insulate the substrate of the first and second ion-selective field effect transistor of the solution to measure.

Alternatively, it is possible to use a wafer structure which provides the insulation so that said transistors are also electrically insulated from the substrate without the need to use encapsulating material in its edges. For example, it is possible to use SOI wafers (thin layer of a semiconductor on an insulating layer) to form the two field effect transistors thereon. To obtain the insulation, once the transistors have been formed, a trench must be made in the semiconductor layer which totally surrounds each one of the transistors, after depositing the insulating layer and finally eliminating the insulating layer from the gate of the transistors and of the wire bonding areas (connection pads). Another form of obtaining insulation is forming the transistors within a region of semiconductor insulated from the rest of the substrate by a p-n junction. In this case, it is necessary to guarantee that the p-n junction is inverse, i.e. that the potential of the p region is more negative than that of the n region.

The manufacturing method of the ion sensor based on differential measurement described here has the advantages, compared with the state of the art, that it can be more easily automated and executed on a large scale, and therefore, allows a considerable reduction in the manufacturing costs thereof.

A third object of the present invention is a conditioning receptacle to store the aforementioned sensor between measurements which makes it possible to extend the lifetime of the sensor indefinitely. The conditioning receptacle will be filled with the reference solution, which allows the solution contained in said microreservoir to be renewed by diffusion through the microchannel.

Since the chips that contain the transistors are encapsulated in a surface which contains metal connection tracks, it is easy to add other components to the sensor (by bonding on the tracks). Some examples would be: 1) A transient voltage suppressor to protect the transistors from electrostatic discharges, e.g. connected between the electrode and the transistor substrate terminal, 2) a thermistor to measure temperature and compensate the thermal drift of the sensor, 3) a memory to store sensor parameters, for example, of the sensitivity to ions and the coefficients of variation with the temperature of each sensor, 4) a polarization and measurement circuit of the ISFET-REFET pair, 5) an analogue-digital converter, 6) a microcontroller, 7) a display to show the measurement data, 8) an interface circuit to communicate the data by a serial protocol (for example, USB standard) with an electronic apparatus (for example a computer or smartphone), 8) a battery, 9) a communications circuit and an antenna to communicate the data wirelessly to another electronic apparatus. A particular combination of these components would give rise to an ion sensor of RFID (Radiofrequency Identification)-type. In this case, the ISFET and the REFET are integrated with a measurement circuit and an analogue-digital converter and with the rest of the circuitry and components typical of a RFID tag. This would make it possible to use a RFID tag reader to obtain the ion measurement data from the exterior of a closed receptacle, the RFID sensor being immersed in the liquid to measure interior the receptacle.

BRIEF DESCRIPTION OF THE FIGURES

FIG. 3.—Shows a particular embodiment of the manufacturing method of the ion sensor based on differential measurement, object of the present invention.

FIG. 4.—Shows a particular embodiment of an alternative manufacturing method of the ion sensor based on differential measurement, object of the present invention.

FIG. 5.

DESCRIPTION OF AN EXAMPLE OF EMBODIMENT OF THE INVENTION

Below, an example of embodiment of the invention is described with illustrative and non-limiting character, making reference to the numbering adopted in the figures.

Figure 1:
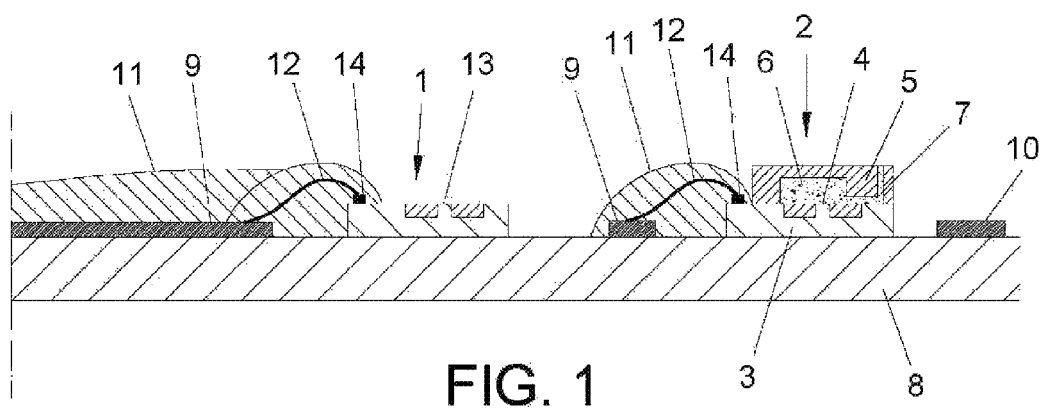
FIG. 1.—Shows a sectional view of a particular embodiment of the ion sensor based on differential measurement object of the present invention.

FIG. 1 shows an example of embodiment of the ion sensor based on differential measurement, object of the present invention, for the specific case wherein it has been designed for measurement of the $H^+$ ion, i.e. for the case wherein the pH of a specific solution is to be measured. Said sensor is formed by an ISFET (1) and a REFET (2), where the REFET (2) is composed in turn of another ISFET (3) the gate (4) whereof is maintained exposed to a constant pH by incorporation of a structure (5) which creates a microreservoir (6) filled with a reference solution (internal solution) with a constant pH. Said microreservoir (6) is connected to the exterior by a microchannel (7). This microchannel in this specific example of embodiment comprises being formed by two sections thereof perpendicular to one another, but it could be formed by a single longitudinal section or have any other configuration.

Both the ISFET (1) and the REFET (2), both integrated in different chips, are in turn fixed on a substrate (8) which has a metal layer defined in the form of connection tracks (9) and an electrode area (10). The chips are partially encapsulated using "chip-on-board"-type techniques, i.e. connection by wire-bonding (soldering of the connection pads (14) of the chips by wire (12)) and protection with glob-top (encapsulating polymer (11)). The encapsulating polymer (11) covers the connection wires (12) and the connection tracks (9) and leaves uncovered the gates of the ISFET (13) and the REFET (4) of, at least partially, the structure (5) which creates the microreservoir (6) and, completely, the outlet of the microchannel (7) of the REFET (2), as well as the electrode area (10).

The REFET chip (2) is formed by the ISFET chip (3) with the structure (5) adhered to its surface forming the microreservoir (6) on the gate (4) of said ISFET (3) and the microchannel (7), so that the walls and the ceiling both of the microreservoir (6) and of the microchannel (7) are of the material of said structure (5), whilst the floor is formed by the surface of the ISFET (3).

Figure 2:
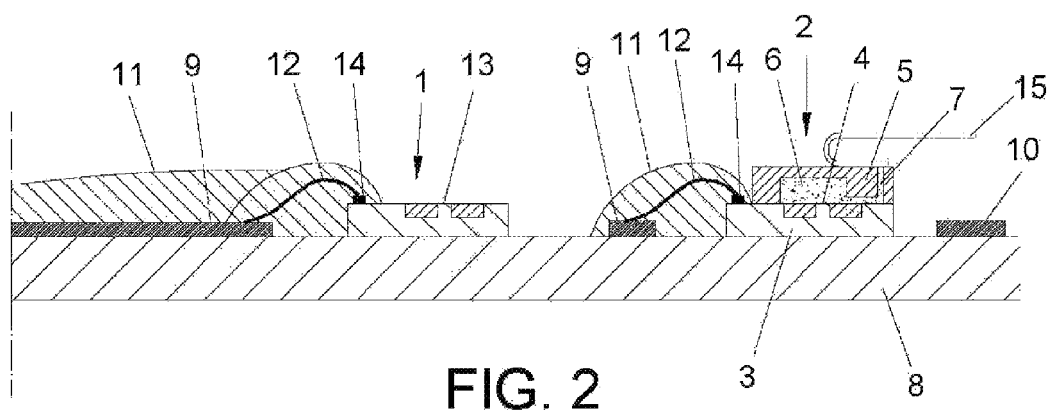
FIG. 2.—Shows a sectional view of the particular embodiment of the ion sensor shown in FIG. 1 whereto sealing means of the microchannel and the microreservoir have been added.

FIG. 2 shows a specific example of embodiment wherein sealing means of the microchannel (7) and of the microreservoir (6) have been adhered to the microchannel (7) outlet. Specifically, an adhesive strip (15) has been adhered, which has a portion without adhesive material so that it can be easily removed by a user. This particular embodiment makes it possible to lengthen the useful life of the sensor since the reference solution in the microreservoir (6) and in the microchannel (7) of the REFET (2) is completely insulated avoiding leaks or the evaporation thereof until the time wherein the sensor is going to be used for the first time and the adhesive strip (15) is removed.

FIG. 3 shows an example of embodiment of the manufacturing method of the sensor described herein. The method is based on the formation of the microreservoir and the microchannel and its bonding on the ISFET using planar technology processes, such as those used for the manufacturing of microfluidic systems. FIG. 3A shows a first wafer (16) where previously and equally spaced it has integrated ISFETs, (20) and connection pads (14) and a second wafer (17) with microreservoirs (18) and microchannels (19) previously made in its lower surface. This second wafer (17) is of a material which means it can be bonded to the first wafer (16). Both wafers (16,17) are aligned so that a microchannel (19) and a microreservoir (18) corresponds to each ISFET (20). The phase wherein the bonding between both wafers (16,17) is performed is shown in FIG. 3B.

In this sense and for the bonding phase between both wafers (14,15), the following process has been provided. The bonding is preferably of chemical type, i.e. by means of the functionalization of the surfaces with molecules which react forming covalent bonds, but other bonding techniques, provided that the geometry of the microchannels (19) is not distorted. Many combinations of materials are known in the state of the art which may be functionalized and chemically bonded. In this regard, one possibility is that the first wafer (16) has the surface of silicon oxide or oxynitride and the second wafer (17) is of polydimethylsiloxane (PDMS), both functionalized by means of an oxygen plasma.

The second wafer (17) is of easy manufacturing with micro-manufacturing techniques used for the implementation of microfluidic systems. It is provided that it has the structure already formed by moulding or some other technique.

The ISFETs (20) are manufactured with a technology that allows them to be insulated from the substrate (8). Said technique is based on the use of SOI wafers and the definition of insulation trenches around the ISFET. In this way it facilitates the encapsulation since it is no longer necessary to protect the chip edges. This allows encapsulating chips with a more reduced area, since the distance of the ISFET gate to the chip edges is no longer critical as there is no danger of the gate being accidentally covered when the encapsulating polymer is applied.

Figure 3A:
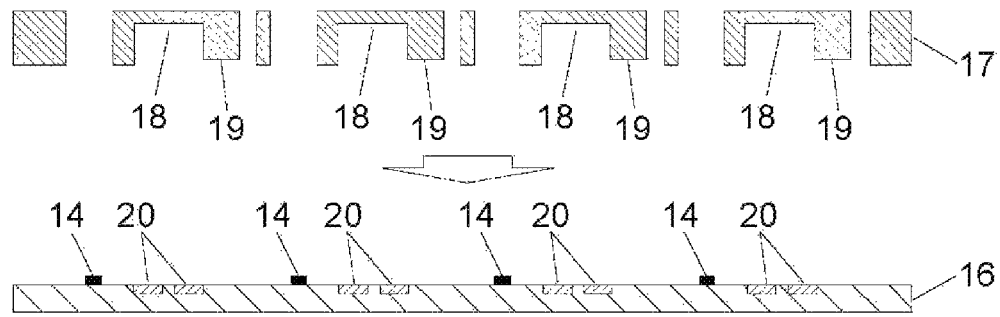
FIG. 3a shows the alignment phase of both wafers.
Figure 3B:
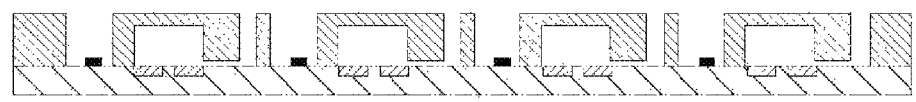
FIG. 3b shows the bonding phase of both wafers.
Figure 3C:
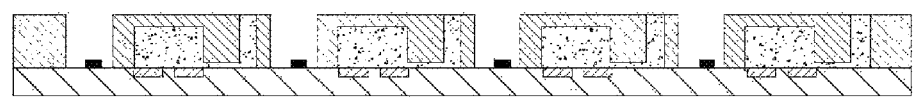
FIG. 3c shows the filling phase of the reservoirs with solution or hydrogel.
Figure 3D:
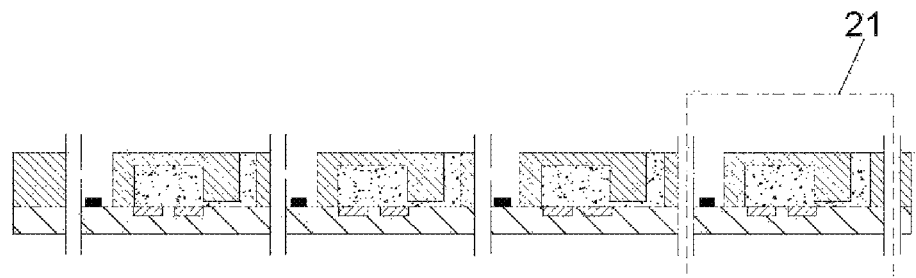
FIG. 3d shows the cutting phase of the resulting wafer into chips.
Figure 4A:
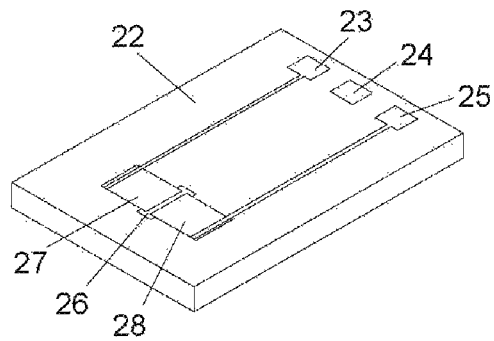
FIG. 4a shows the ISFET.
Figure 4B:
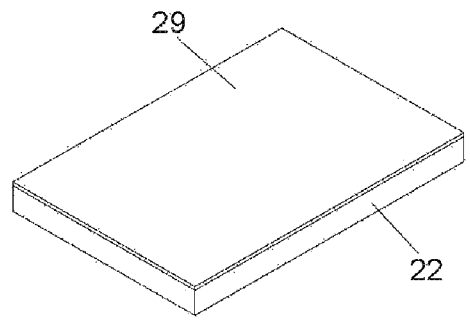
FIGS. 4b to 4g show the subsequent bonding phases of layers of polymer alternated with photolithography phases to configure the microreservoir and the microchannel.
Figure 4C:
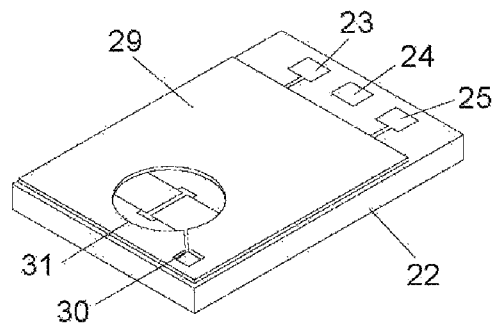
Figure 4D:
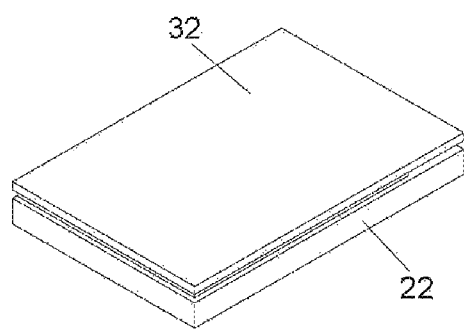
Figure 4E:
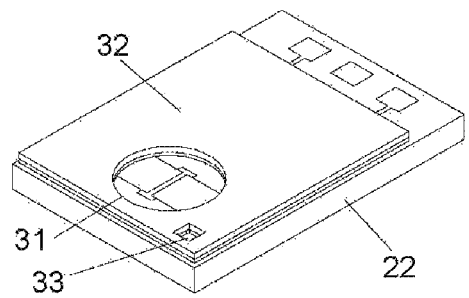
Figure 4F:
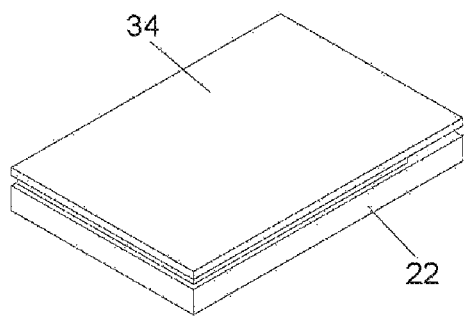
Figure 4G:
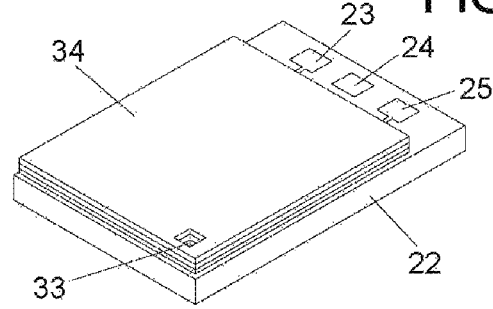

After cutting the wafers (16, 17) into individual chips (21), as shown in FIG. 3D, they can be encapsulated by automatic techniques similar to those established in the microelectronic industry such as "chip on board". This consists of adhering the chips (21) to a substrate (typically a printed circuit board), connecting them by wire bonding (12) and protecting the assembly with an encapsulating polymer (11). The variation in this case with respect to the standard technique is that the encapsulating polymer (glob-top) does not cover the entire chip, but it is only applied on the area of the connection wires. The sensor with all its components already assembled on the substrate is shown in FIG. 3D.

FIG. 4 shows another alternative manufacturing technique of the REFET wherein a REFET is obtained by layer addition starting from a chip where an ISFET is integrated. FIG. 4a shows an ISFET on a chip (22) wherein said ISFET comprises a source pad (23) connected to the source (27) of the transistor, a drain pad (25) connected to the drain (28) of the transistor and a substrate pad (24) (all of them form the connection pads (14) of the ISFET) and a gate (26). Subsequently, a first layer (29) of polymer is deposited by bonding or a pre-polymer is deposited by centrifugation and is then heat cured, as shown in FIG. 4b. This layer of polymer (29) is structured (FIG. 4c) by lithography creating the microchannel (30) and the microreservoir (31) and leaving the connection pads (23,24,25) free of polymer. Subsequently, and as shown in FIG. 4d, a second layer (32) of polymer is bonded by lamination on the first layer (29) of polymer. Again, this second layer (32) of polymer is structured by photolithography increasing the volume of the microreservoir (31) and closing the microchannel (30) (FIG. 4e) but leaving free the outlet orifice (33) of the microchannel (30). Finally, a third layer (34) of polymer is bonded and it is structured by lithography (FIGS. 4f and 4g) thus the microreservoir (31) remains closed and only the outlet orifice (33) of the microchannel (30) remains open. The three layers of polymer (29,32,34), which may be SU8, define the microreservoir (31) and the microchannel (30) which in turn is connected to the exterior through its outlet orifice (33). This outlet orifice (33) allows the filling to wafer level of the microchannel (30) and the microreservoir (31) with hydrogel or with any reference solution.

The structure of an ISFET is similar to that of a MOS transistor (diffusion of drain and source in a doped semiconductor substrate) with the difference that it does not have a gate electrode and the gate dielectric is exposed. So that the ISFET and REFET devices function correctly they must have the gate dielectric in contact with the solution, the ISFET gate dielectric with the solution that one wants to measure and the REFET gate dielectric with the reference solution, but they must have the drain, the source and the substrate insulated from the respective solutions. To guarantee this, a layer of insulating material is deposited on the chip surface during its manufacturing (at wafer level), and the chip edges are protected with the encapsulating polymer during the encapsulating process. Alternatively, it is possible to use a manufacturing technology that makes it possible to electrically insulate the device substrate from the chip edges, so that it is not necessary to protect them with polymer, for example using SOI (Silicon on insulator) wafers. To be able to use the "chip-on-board" standard encapsulation technique it is possible to use the two ways of insulating the substrate, but the first requires a large space (~2 mm) between the ISFET gate and the edge of the chip in all directions, which makes it necessary to have large, and therefore expensive, chips. The second option, via the se of SOI wafers becomes more suitable for the manufacturing of the ISFET-REFET sensor described herein, since it allows the encapsulation of chips of reduced area, only requiring that the separation is large in one direction (for example, in a rectangular chip the ISFET gate would be situated at one end of the chip and the connection pads to protect with glob-top at the other end of the chip).

An interesting variant of the REFET is the one where microreservoir and the microchannel are filled with a hydrogel. The advantages in this case are of avoiding problems of bubble formation in the microchannel and the microreservoir (which could cause malfunctioning) and the possibility of storing the sensor dry until its use. The hydrogel would be soaked in the reference solution and would perform the same function as the internal solution without hydrogel. This material is very hygroscopic, so that it would take a lot longer to dry if the sensor was left outside the solution. In the event of totally drying, it could be easily rehydrated by re-immersing in distilled water or in reference solution without the danger of bubbles forming.

Figure 5A:
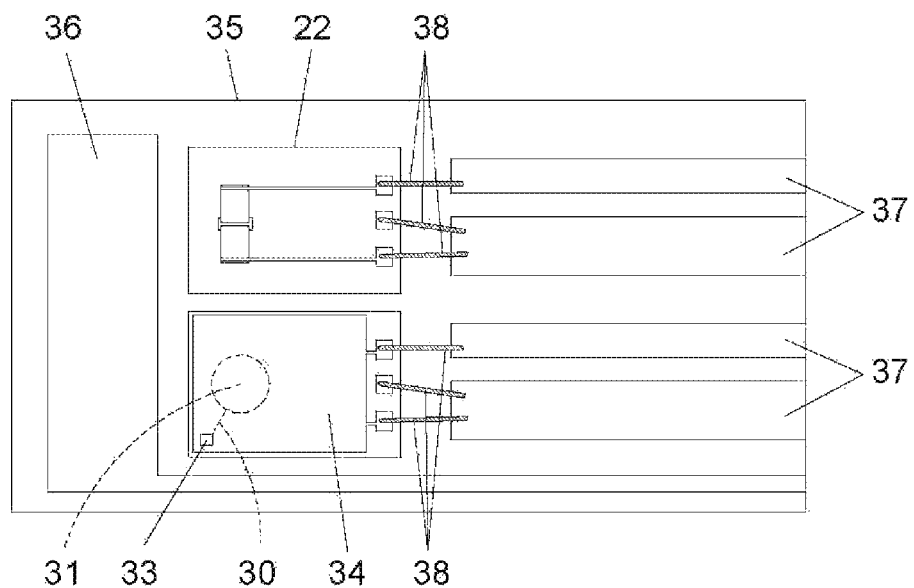
—FIG. 5a shows a plan view of an example of embodiment of the sensor with all its components.
Figure 5B:
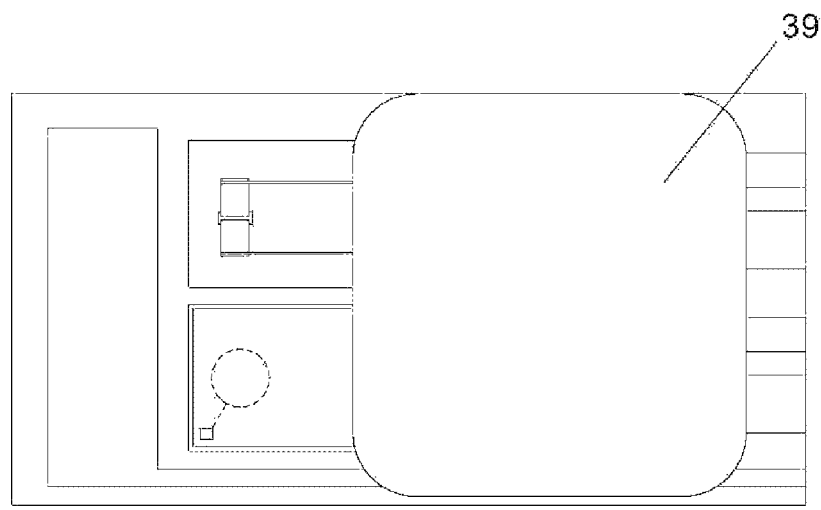
FIG. 5b shows the sensor of FIG. 5a wherein the encapsulating polymer has been added.

FIG. 5 shows a plan view of an example of embodiment of a pH sensor in accordance with the present invention. FIG. 5a shows a PCB substrate (35) wherein an ISFET and a REFET such as those described in FIG. 4, an electrode (36) and connection tracks (37) have been fixed. Said tracks are connected both to the ISFET and the REFET by the connection pads (23,24,25) by wire bonding (38). FIG. 5b shows the sensor of FIG. 5a wherein the encapsulating material (39) has been deposited, which partially covers both the ISFET and the REFET and totally covers the connections thereof with the connection tracks (37).

Finally, it has been provided to integrate in a single chip the ISFET and the REFET and even further reducing the sensor's cost.

Figure 6A:
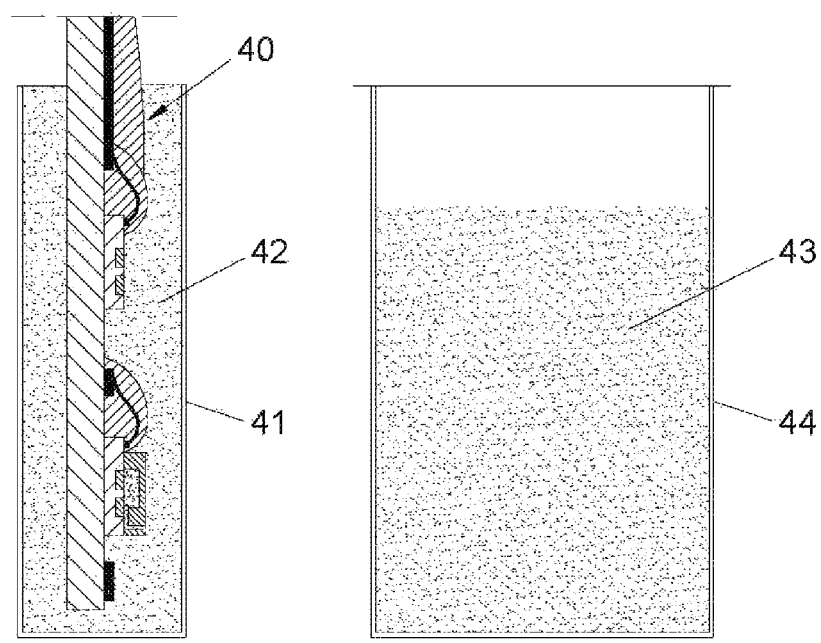
FIGS. 6a-6b.—Shows an example of the use of the ion sensor of FIG. 1 in the measurement of a determined ion concentration of any solution.
Figure 6B:
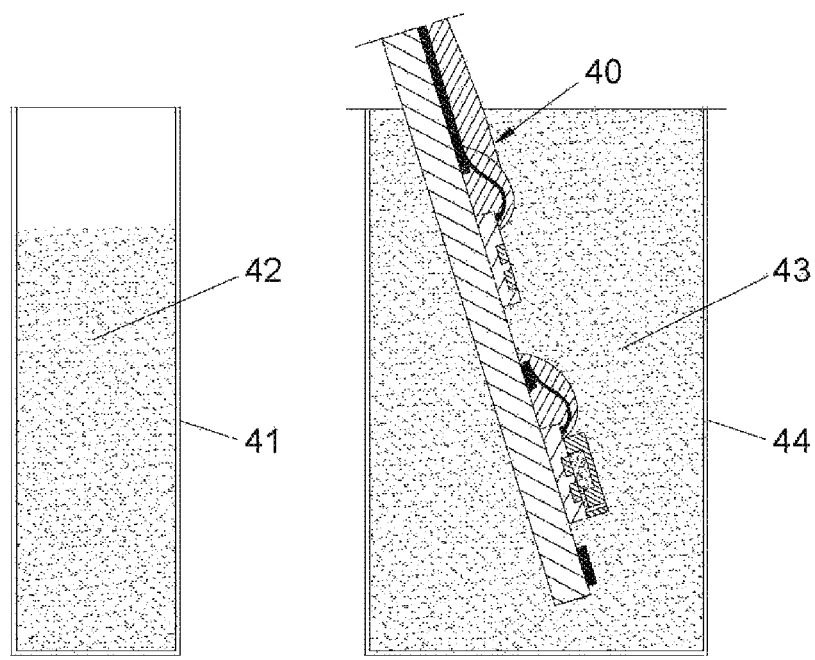

Another object of the invention is also an ion measurement method using an ISFET/REFET sensor described. When it is not being used, the sensor (40) is introduced in a conditioning receptacle (41) filled with a reference solution (42) (FIG. 6a). This reference solution (42) also serves as calibration solution as its ion concentration is known. Once the sensor (40) has been introduced for the first time in the reference solution (42) and sufficient time has been given so that the microreservoir (6) fills or is soaked with said solution (42), said sensor (40) is removed from the conditioning receptacle (41), it is rinsed and immersed in the solution to measure (43) situated within a measurement receptacle (44), keeping the microreservoir (6) of the REFET filled with the reference solution (42) (FIG. 6b). After its use, the sensor (40) is cleaned and is re-inserted in the conditioning receptacle (41) so that the microreservoir (6) solution is balanced with a receptacle solution and returns to its original ion concentration. The sensor (40) would function correctly whenever the time of use is less than the time wherein the sensor (40) is immersed in the reference solution (42) within the conditioning receptacle. The present invention is novel in that the sensor (40) is maintained in the conditioning receptacle (41) between one measurement and the next, which means that the sensor does not have a limited lifetime due to contamination of the reference solution or of diffusion of its components towards the exterior. An added advantage is that as the conditioning receptacle (41) is filled with the reference solution (42), whose ion concentration is fixed (for example a buffered solution to maintain the constant pH in the event that the ISFET is selective to the pH and the REFET is constructed with a pH-selective ISFET), the sensor can be calibrated before its removal in the same way transparent to the user.

Among the multiple applications that can be given to the ion sensor object of the present invention is that of integrating the sensor in a self-diagnostic medical device by the measurement of, for example, ions in urine, which may be of interest for controlling diseases such as lithiasis and osteoporosis. Another possible application would be the measurement of vaginal pH for birth control, where the measurement made by the sensor was transmitted to a mobile device (for this the sensor object of the present invention must have a communication interface with the mobile device). Another possible application for the sensor would be the monitoring of ions in cell cultures. Introducing the sensor within the culture medium, it would be possible to continuously control the state of the cells without the need to open the receptacle lid. In this case the measurement could be transmitted to a wireless communication system integrated in the sensor.

The invention claimed is:

1. An ion sensor based on differential measurement, comprising:
a first ion-selective field effect transistor and a second ion-selective field effect transistor, electrically connected by connection tracks to an ion measurement system and each ion-selective field effect transistor having a gate;
an electrode arranged to be in contact with a solution to measure;
at least one chip on the surface whereof are integrated the ion-selective field effect transistors;

a structure adhered on the first ion-selective field effect transistor configured to create a microreservoir on the gate of only the first ion-selective field effect transistor, the microreservoir being filled with a reference solution, wherein the first ion-selective field effect transistor is arranged to be in contact with the reference solution and the second ion-selective field effect transistor is in contact with a solution to measure;

at least one microchannel having an outlet, the at least one microchannel connecting the microreservoir with the exterior of the structure, the at least one microchannel being filled with the reference solution;

a substrate whereon is integrated the at least one chip, the connection tracks and the electrode; and, an encapsulating material which completely insulates the connection tracks and partially insulates the first and second ion-selective field effect transistors of the solution to measure, wherein the gates of the first and second ion-selective field effect transistors and the outlet of the microchannel are uncovered.

2. The ion sensor based on differential measurement, according to claim 1, wherein the reference solution is contained in a hydrogel.

3. The ion sensor based on differential measurement, according to claim 1, wherein the first ion-selective field effect transistor is integrated in a first chip and the second ion-selective field effect transistor is integrated in a second chip.

4. The ion sensor based on differential measurement, according to claim 3, wherein connection of connection points of the chip with the connection tracks is performed via wire bonding.

5. The ion sensor based on differential measurement, according to claim 1, wherein the first ion-selective field effect transistor and the second ion-selective field effect transistor are integrated in the same chip.

6. The ion sensor based on differential measurement, according to claim 1, wherein the first and second ion-selective field effect transistor, the connection tracks, the electrode and a part of the measurement circuit are integrated in the same chip.

7. The ion sensor based on differential measurement, according to claim 1, wherein the structure adhered on the first ion-selective field effect transistor is at least partially of a gas-permeable material and impermeable to the reference solution.

8. The ion sensor based on differential measurement, according to claim 7, wherein the microchannel is a notch made in the chip whereon the first ion-selective field effect transistor is integrated.

9. The ion sensor based on differential measurement, according to claim 1, wherein the microchannel forms part of the structure adhered on the first ion-selective field effect transistor.

10. The ion sensor based on differential measurement, according to claim 9, wherein the microreservoir has a volume between 0.001 $mm^3$ and 1 $mm^3$, and the microchannel has a section of between 1 square micrometer and 10000 square micrometers and a length between 10 microns and 1 mm.

11. The ion sensor based on differential measurement, according to claim 1, wherein the microchannel has removable and external sealing means to seal the content of the microreservoir and microchannel.

12. The ion sensor based on differential measurement, according to claim 11, wherein the chips are manufactured from silicon on insulator.

13. A conditioning receptacle for an ion sensor based on differential measurement as in claim 12, wherein the conditioning receptacle comprises the reference solution to fill or regenerate the microreservoir and the microchannel with the reference solution.

14. The ion sensor based on differential measurement, according to claim 1, wherein the ion sensor is placed in a conditioning receptacle that contains the reference solution to fill or to regenerate the microreservoir and the microchannel.

15. Manufacturing method of the ion sensor based on differential measurement, described in claim 1, wherein it comprises the following phases:

integrating a plurality of first ion-selective field effect transistors equally spaced on a first wafer;

coupling a structure of bondable material on the first wafer, creating a plurality of equally spaced microreservoirs and microchannels in correspondence with the first ion-selective field effect transistors, so that each microreservoir is situated in correspondence and aligned with each first ion-selective field effect transistor;

cutting the first wafer transversally creating chips, where each chip comprises a first ion-selective field effect transistor and a structure with a microreservoir and at least one microchannel;

fixing on a substrate a chip, at least one second field effect transistor, the electrode and the connection tracks;

connecting the connection tracks to the first and second field effect transistor and encapsulating the first and second field effect transistor and the connection tracks.

16. The method of manufacturing an ion sensor based on differential measurement, according to claim 15, further comprising adding a plurality of layers of bondable material subjected to a photolithography process on the wafer, to generate the structure of bondable material with the microreservoirs and microchannels.

17. The method of manufacturing an ion sensor based on differential measurement, according to claim 15, further comprising subjecting the structure of bondable material to a recessing process for the creation of the microreservoirs and the microchannels.

18. The method of manufacturing an ion sensor based on differential measurement, according to claim 15, wherein encapsulating material is additionally deposited on edges of the first and second ion-selective field effect transistor to electrically insulate the substrate of the first and second ion-selective field effect transistor.

19. The method of manufacturing an ion sensor based on differential measurement, according claim 18, wherein different ion-selective membranes are fixed on the second ion-selective field effect transistors.

* * * * *